US00PP29705P3

(12) United States Plant Patent
Infante Espineira

(10) Patent No.: US PP29,705 P3
(45) Date of Patent: Sep. 25, 2018

(54) NECTARINE TREE NAMED 'ANDES NEC-4'

(50) Latin Name: *Prunus persica* (Nectarine)
Varietal Denomination: Andes Nec-4

(71) Applicants: UNIVERSIDAD DE CHILE, Santiago (CL); VIVEROS ASOCIADOS CHILE LIMITADA, Santiago (CL)

(72) Inventor: Rodrigo Arturo Infante Espineira, Paine (CL)

(73) Assignees: UNIVERSIDAD DE CHILE, Santiago (CL); VIVEROS ASOCIADOS CHILE LIMITADA, Santiago (CL)

( * ) Notice: Subject to any disclaimer, the term of this patent is extended or adjusted under 35 U.S.C. 154(b) by 18 days.

(21) Appl. No.: 14/999,839

(22) Filed: Jul. 7, 2016

(65) Prior Publication Data

US 2018/0014443 P1 Jan. 11, 2018

(51) Int. Cl.
*A01H 5/08* (2018.01)

(52) U.S. Cl.
USPC ..... Plt./188

CPC ..... *A01H 5/0856* (2013.01)

(58) Field of Classification Search
USPC ..... Plt./188
See application file for complete search history.

(56) References Cited

U.S. PATENT DOCUMENTS

PP25,940 P2 * 9/2015 Meerow ..... A01H 5/02
Plt./402

* cited by examiner

*Primary Examiner* — Anne Marie Grunberg
(74) *Attorney, Agent, or Firm* — Greer, Burns & Crain, Ltd.

(57) ABSTRACT

A new and distinct variety of nectarine tree named "Andes Nec-4" which has fruit that is similar to the '6B-170' nectarine that is white in flesh color. The variety is distinguished from the '6B-170' by reaching out higher content of soluble solids, by more extended red blush of the nectarine surface, by slower pulp softening rate during the last two weeks before the commercial harvest, by a higher postharvest life potential, and by a balanced acid/sweet flavor. 'Andes Nec-4' can maintain its quality after 40 days in cold storage.

6 Drawing Sheets

Species: *Prunus persica* (Nectarine).

Cultivar name: 'ANDES NEC-4'.

This new cultivar resulted from controlled hybridization between the nectarine '6B-170' (♀) and the peach '78-R-121' (♂) performed in 2009 at Maipú, Metropolitan Region, Chile (latitude –33°78' S, longitude –70°64' S, altitude 210 m above level. This tree was first asexually propagated on July 2012, and tested on a block of 10 cloned trees in the same experimental station at Maipú and in El Tambo, VI region of Chile. The new variety differs of his non-patented female progenitor '6B-170', due it reaches higher content of soluble solids, reaching up to 17.5 whereas '6B-170' seldom reaches more than 11.0; also because the blush of 'Andes Nec-4' covers 90-100% of its surface, while '6B-170' seldom covers more than 60%. '6B-170' is also a white fleshed nectarine that in postharvest lasts no more than 14-21 days in good conditions, whereas 'Andes Nec-4' can maintain quality after 40 days in cold storage. On regard of its non-patented male progenitor, the selection '78-R-121' is less productive than 'Andes Nec-4', it has high acidity and yellow flesh, whereas 'Andes Nec-4' is a balanced sweet/acid cultivar, reaching ratios around 10 to 12.

'AndesNec-4' belongs to the group of "melting" varieties which is different to those classified in the "non-melting" group, which are peaches for the canning industry, that show a gummy texture. In the group classified as "melting" it is possible to find some varieties that soften in very few days and other that show a very subtle softening, but they also soften. In the case of "Andes Nec-4", its firmness is maintained during post-harvest time, that means that the softening rate is slow, being different to most of the traditional melting flesh type varieties (Shinya, et. al., 2013).

Distinctive Characteristics of the Variety:

Semi upright plant growth, medium to high vigor. Fruit round, symmetrical, solid 90 to 100% red blush. Harvest period 30 days before 'August Red'.

This cultivar main feature is a slow pulp softening rate during the last two weeks before the commercial harvest. This feature enables delaying harvesting, pursuing the increase of the fruit size and soluble solids content without affecting their postharvest life potential. Secondly it shows a high postharvest life potential, which can reach up to 40 days at 0° C. while maintaining its initial sensory quality. From a sensory point of view this is a variety of medium to low acidity with a balanced sweetness/acidity ratio and in general an average overall sensory quality. The variety is not susceptible to "chilling injury" and therefore can be used for exporting to distant markets.

BRIEF DESCRIPTION OF THE FIGURES

The drawings of the nectarine of the present variety are color photographs.

Figure 1:
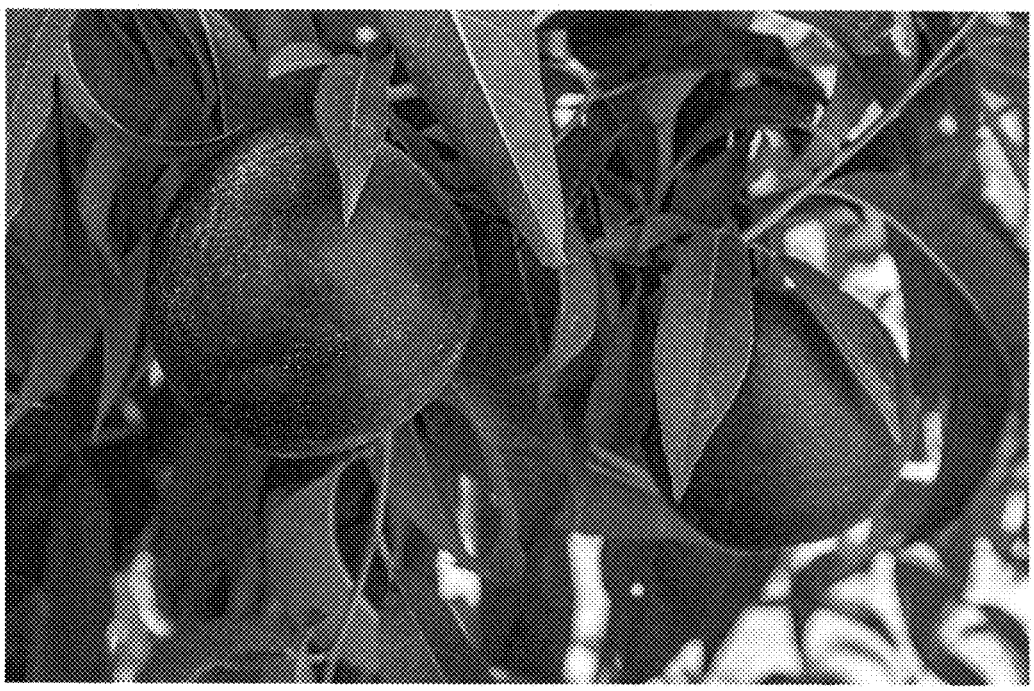
FIG. 1 shows typical specimens of the whole fruit in skin color and form, on tree, and typical leaves.
Figure 2:
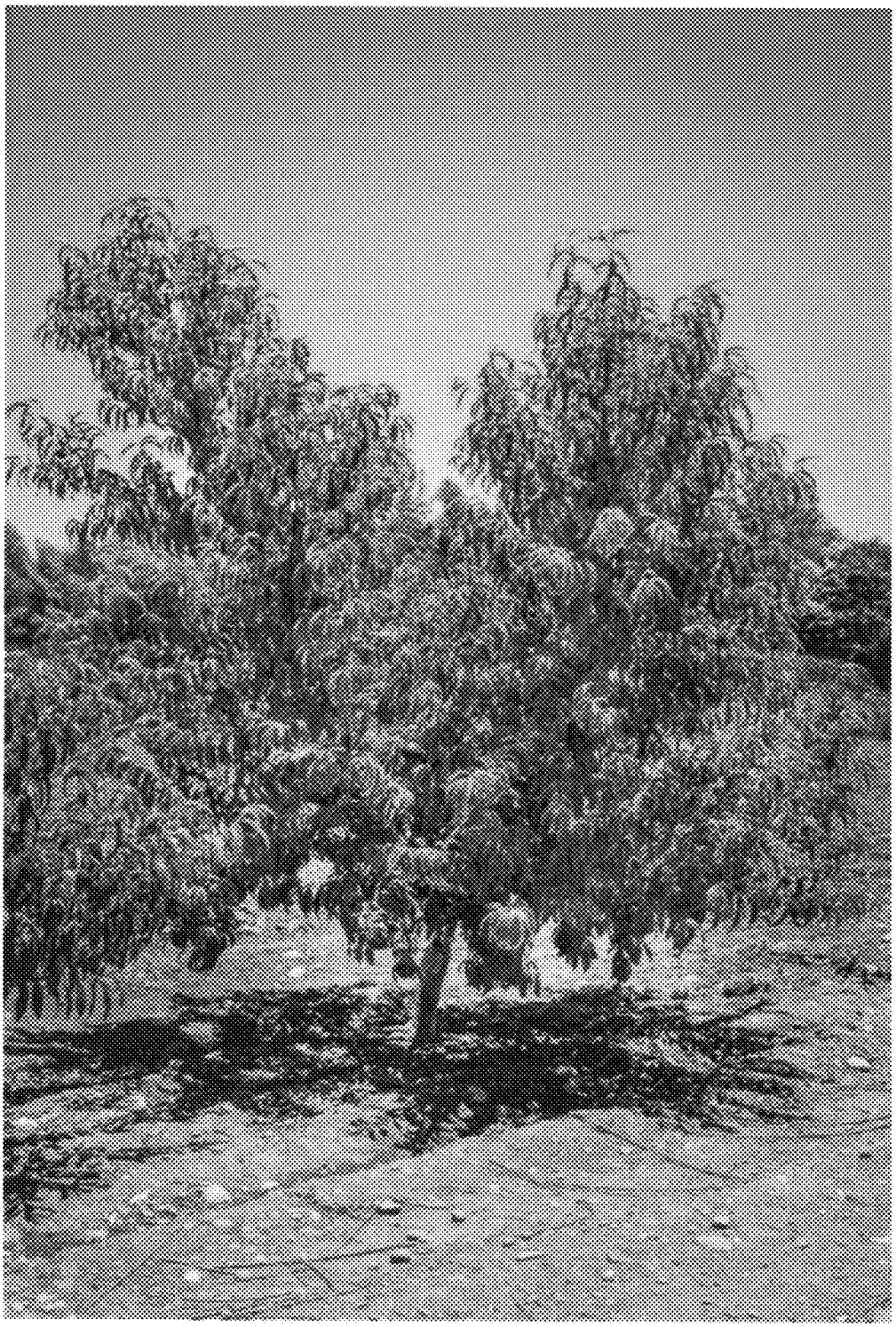
FIG. 2 shows a nectarine tree named 'Andes Nec-4'.
Figure 3A:
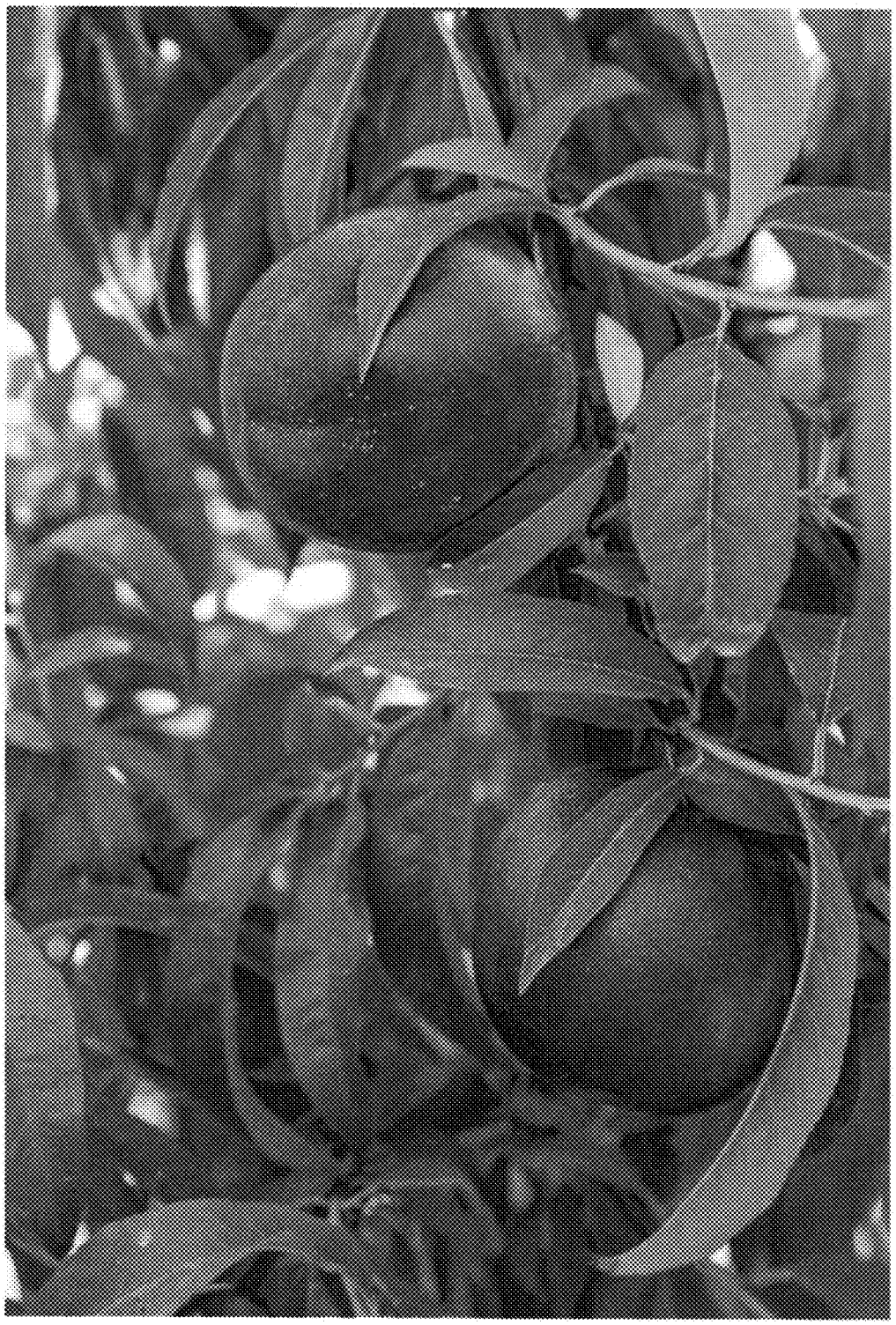
FIGS. 3(*a*) and 3(*b*) are two photographs that show two enlarged views of typical specimens of the fruit and leaves on the tree of FIG. 2.
Figure 3B:
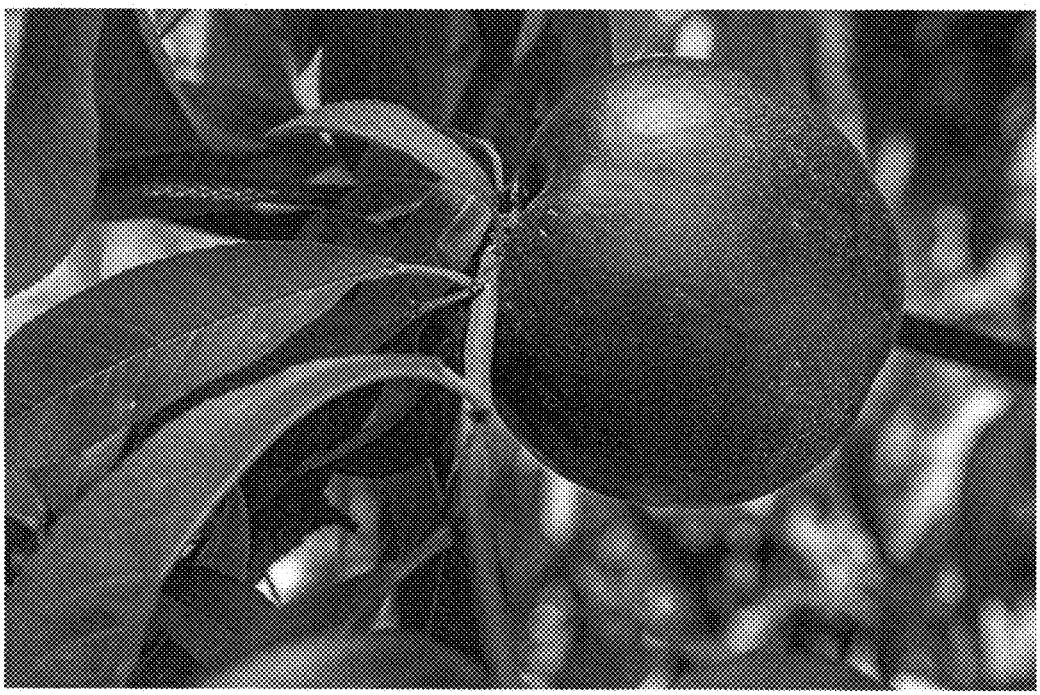
Figure 4:
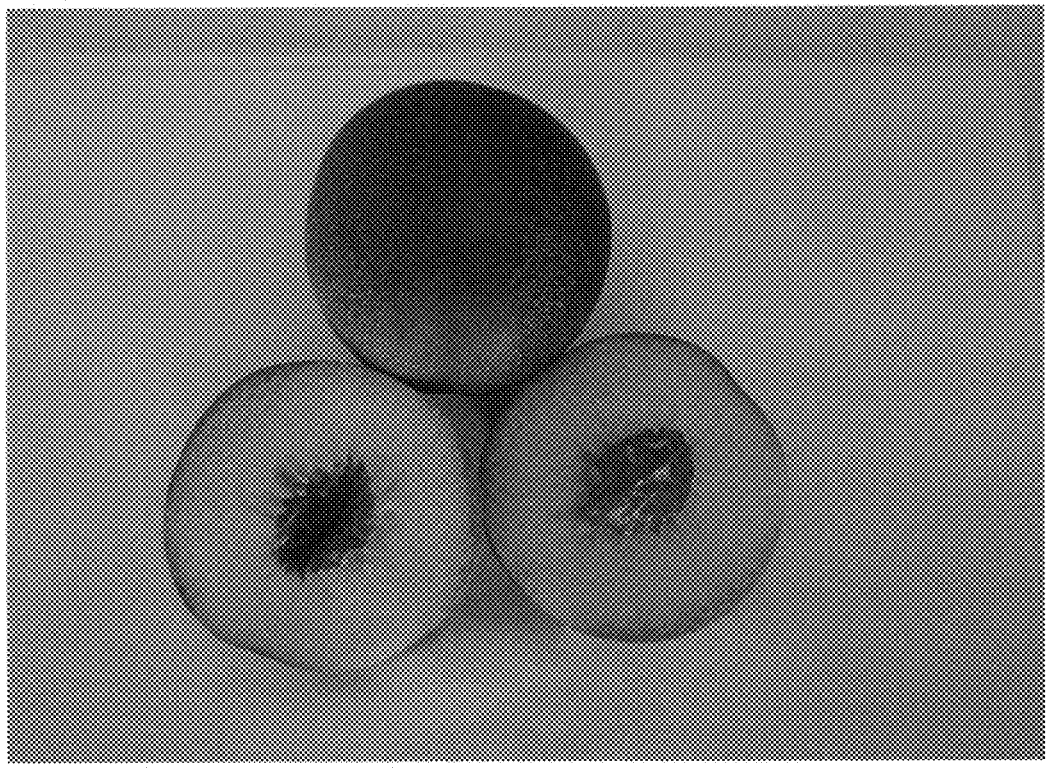
FIG. 4 is a photograph of the fruit flesh and stone next to the whole fruit.
Figure 5:
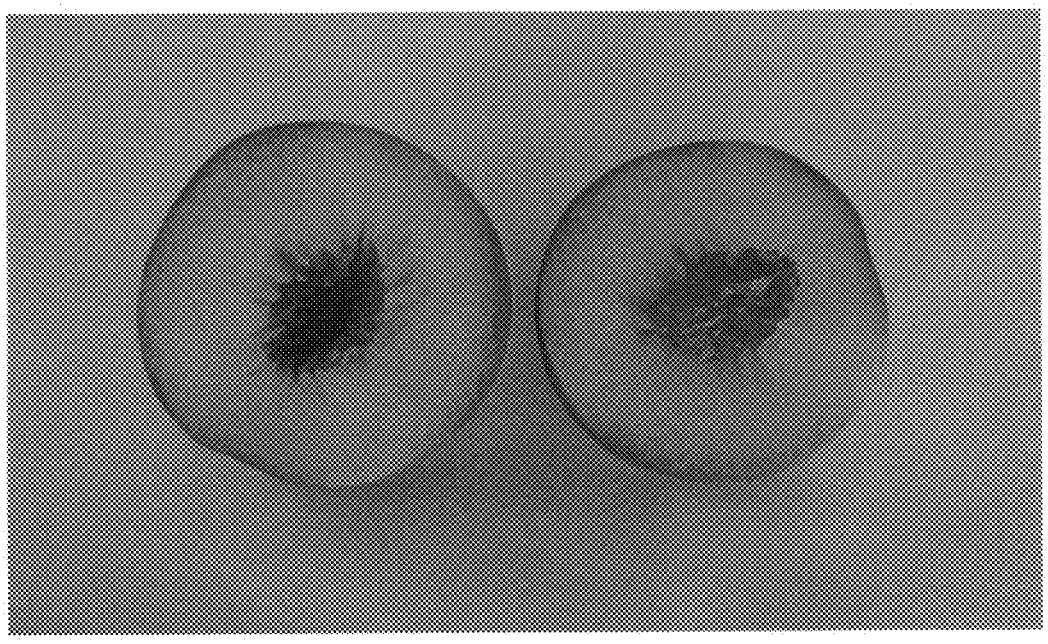
FIG. 5 is a photograph of the fruit flesh and stone.

Characterization of 'Andes Nec-4' Nectarine.

Color descriptions below are based on evaluations with a Minolta CR-400 colorimeter al CIE D65/0° illumination/viewer conditions. The color parameters correspond to the uniform color space CIELAB, derived from McGuire (1992). Two color coordinates, a* and b*, as well as a psychometric index of lightness, L*, are defined. The L* is a measurement of luminosity, i.e., the equivalence of each color on the gray scale, ranging from 0 (black) to 100 (White). The a* takes positive values (0 to +60) for reddish colors and negative values (0 to −60) for the greenish ones, whereas the b* takes positive values (0 to +60) for yellowish colors and negative values (0 to −60) for the bluish ones. This is much more precise and repeatable analysis of color than obtained by using color charts. Where a reasonably close match could be discerned, The Munsell Color Chart is also referenced.

Tree:

1. *Size*.—Medium, similar to 'Bonanza'. An 8 year old tree is 4.3-4.5 m high shaped as an open vase, 2.5-3.0 of diameter.
2. *Vigor*.—Medium, similar to 'J.H. Hale'. Shoots reach 20 to 50 cm on regular spring/summer growing period.
3. *Habit*.—Horizontal, like 'Albertina'. It is well adapted to open vase training.
4. *Type of bearing*.—On spurs and long shoots.
5. *Spur length*.—4.2 cm in average.
6. *Flowering shoot thickness* (*excluding brindilles*).—Medium, similar to 'Redhaven'. The typical and observed flowering shoot diameter is 0.4-0.6 mm.
7. *Flowering shoot length of internodes*.—Medium, similar to 'Redhaven'. The typical and observed flowering shoot internode length is 2.4-3.0 cm.
8. *Flowering shoot coloration*.—There is present anthocyanin coloration in the zone exposed to sunlight, reaching a light red color, that in coordinates a*, b* and L* of the CIELab space color (McGuire, 1992) corresponds to 46.1, 12.0, and 10.9, respectively, but in the lower part of the shoot the anthocyanin coloration is weak, similar to 'Springtime', reaching a light brown color, that in coordinates a*, b* and L* of the CIELab space color (McGuire, 1992) corresponds to 37.9, 8.2, and 12.1, respectively. (McGuire, R. G. 1992. Reporting of Objective Color Measurements. Hortscience. 27(12): 1254-1255).
9. *Flowering shoot density of flower buds*.—Medium, similar to 'Michelini', reaching in an average year 25-36 flowers/30 cm long shoot.
10. *Flowering shoot*.—General distribution of flower buds: in groups of two or more, similar to 'Redhaven'.
11. *Flowering bud coloration*.—3.4R 3.9/7.7 (LRV 11) Munsell color, determined by visual observation.
12. The trunk of an 8-year old tree shows a 12-15 cm diameter, measured on 50 cm above the ground, the bark texture is smooth with few lenticels, and the bark color is dark brown, that in coordinates a*, b* and L* of the CIELab space color (*McGuire,* 1992) corresponds to 44.0, 3.1, and 10.2, respectively.
13. *Number of bark lenticels*.—5 lenticels per $cm^2$ in average.
14. *Size of bark lenticels*.—Approximately 0.6 mm in width, approximately 0.15 mm in height.
15. *Bark lenticels color*.—1.5Y 8.1/5.3 (LRV 58) Munsell color, determined by visual observation.
16. The primary branches diameter reaches 6-8 cm in an 8-year old tree, and the color is light brown, that in coordinates a*, b* and L* of the CIELab space color (*McGuire,* 1992) corresponds to 49.7, −2.0, and 23.6, respectively.
17. *Vegetative buds shape and color*.—Acuminate, 4.8-7.5 mm length, color brown that in coordinates a*, b* and L* of the CIELab space color (McGuire, 1992) corresponds to 98.3, −6.6, and 29.3, respectively.
18. *Position of vegetative bud in relation to one year old shoot*.—Slightly held out.
19. AndesNec-4 is self-fertile.
20. *Number of chilling hours required*.—600 hours.

Flower:

21. *Type*.—It has a showy type, similar to 'Robin', reaching a whole diameter of 2.7 to 3.0 cm, and ovary is settled 0.45 to 0.55 cm low the calyx Showy, similar to 'Robin'.
22. *Calyx color of inner side* (*opened flower, before falling of petals*).—Pale yellow, similar to 'Robin', the color is classified as in coordinates a*, b* and L* of the CIELab space color (McGuire, 1992) corresponds to 60.1, 12.4, and 25.9, respectively.
23. *Corolla predominant color* (*inner side*).—Medium pink, similar to 'Fuzalode', classified in coordinates a*, b* and L* of the CIELab space color (McGuire, 1992) corresponds to 87.2, −1.1, and 10.7, respectively.
24. *Petal shape*.—Round, similar to 'Springtime'.
25. *Petal size*.—Medium, similar to 'Robin', 1.1 to 1.6 cm diameter.
26. *Petals number*.—Five, similar to 'Redhaven'.
27. *Arrangement of petals*.—Free.
28. *Petal coloration*.—The petal color is classified in coordinates a*, b*, and L* of the CIELab space color (McGuire, 1992) corresponds to 87.2, −1.1, and 10.7, respectively.
29. *Stamens position compared to petals*.—Above 0.5 to 1.0 mm, similar to 'Redhaven'.
30. *Stamen number and length*.—There are 35-40 stamens per flower in average 1 cm, of white-cream color, in coordinates a*, b* and L* of the CIELab space color (McGuire, 1992) corresponds to 92.2, −3.6, and 9.8, respectively.
31. *Stigma position compared to anthers*.—Same level, similar to 'Crimson Gold'.
32. *Pistil*.—There is normally 1 per flower, 12 mm length and white cream color according to in coordinates a*, b* and L* of the CIELab space color (McGuire, 1992) corresponds to 62.7, 3.5, and 10.0, respectively.
33. *Anthers pollen*.—Present and abundant, similar to 'Redhaven', in number 34 to 40, and the characteristic color of anthers is classified in coordinates a*, b* and L* of the CIELab space color (McGuire, 1992) corresponds to 85.2, 4.2, and 44.5, respectively.

34. *Ovary shape*.—Pubescence is absent, similar to 'Fuzalode', and round shape.
35. *Ovary color*.—4GY 8.5/5.1 (LRV 66) Munsell color, determined by visual observation.

Leaf:

36. *Leaf blade length*.—Long, reaching 12-16 cm long.
37. *Leaf blade width*.—Medium, reaching 4.5-5.5 cm width.
38. *Leaf blade*.—Ratio length/width: Medium, similar to 'Early Sungrand', reaching a ratio of 3.5.
39. *Leaf blade incisions of margin*.—Shallow serrate.
40. *Leaf blade shape in cross section*.—Flat, similar to 'Mayred'.
41. *Leaf blade recurvature of apex*.—Absent, similar to 'Merril Sundance'.
42. *Leaf blade angle at base*.—Acute, less than 90°, similar to 'Springtime'.
43. *Leaf blade angle at apex*.—Medium to acute, similar to 'Earlyred'.
44. *Leaf blade color*.—Green, similar to 'Robin', classified in coordinates a*, b* and L* of the CIELab space color (McGuire, 1992) corresponds to 37.5, −7.9, and −16.1, respectively on the upper surface and in coordinates a*, b* and L* of the CIELab space color (McGuire, 1992) corresponds to 58.5, −5.7, and −14.1, respectively, in the lower surface.
45. *Petiole length*.—Short, similar to 'Redhaven', reaching 2-3 mm.
46. *Petiole*.—Two to four nectaries present, similar to 'Redhaven'.
47. *Petiole shape of nectaries*.—Reniform, similar to 'Redhaven'.
48. *Petiole predominant number of nectaries*.—More than two, similar to 'Everts'.

Fruit:

49. *Fruit size*.—Medium, similar to 'Sunhaven', ranging between 150 to 210 g.
50. *Fruit shape* (*in ventral view*).—Round, similar to 'Redwing'. The observed fruit length parallel to the suture is 5.5 to 6.5 cm and width perpendicular to the suture is 6.0 to 7.0 cm.
51. *Fruit shape of pistil end*.—Plane, similar to 'Redhaven'.
52. *Fruit symmetry* (*viewed from pistil end*).—Symmetric, similar to 'Morettini'.
53. *Fruit prominence of suture*.—Weak, similar to 'Redhaven'.
54. *Fruit depth of stalk cavity*.—Shallow, similar to 'Robin', ranging between 5-6 mm.
55. *Fruit width of stalk cavity*.—Medium, 1.8-2.0 cm.
56. *Length of stalk on fruit*.—0.8 cm in average.
57. *Fruit ground color*.—Greenish yellow, classified in coordinates a*, b* and L* of the CIELab space color (McGuire, 1992) corresponds to 61.9, 5.4, and 30.2, respectively, similar to 'Precoce de Hale' when is mature.
58. *Fruit over color*.—Present.
59. *Fruit*.—Hue of over color: 26.42°, Red, classified as CIELAB, similar to 'Red Diamond'.
60. *Fruit pattern of over color*.—Solid pattern, similar to 'Flavorcrest'.
61. *Fruit extent of over color*.—Large, reaching 100%.
62. *Fruit pubescence*.—Absent.
63. *Number of fruit lenticels*.—100 lenticels per $cm^2$ in average.
64. *Size of fruit lenticels*.—68.4 μm in average.
65. *Fruit thickness of skin*.—Medium, similar to 'Madame Girard'.
66. *Fruit adherence of skin to flesh*.—Strong, similar 'Babygold 5'.
67. *Fruit firmness of pulp*.—Firm, reaching 11.5 to 13.0 pounds when mature.
68. *Fruit ground color of flesh*.—White, classified in coordinates L, Hue and Chroma of the CIELab space color (McGuire, 1992) corresponds to 78.4, 64.7 and 19.5, respectively.
69. *Fruit anthocyanin coloration directly under skin*.—Weakly expressed.
70. *Fruit anthocyanin coloration of flesh*.—Absent or very weakly expressed, similar to 'Robin'.
71. *Fruit anthocyanin coloration around stone*.—Absent or very weakly expressed, similar to 'Springtime'.
72. *Fruit texture of the flesh*.—Not fibrous, melting flesh type, similar to 'Redhaven'.
73. *Fruit flesh coloration next to the stone*.—4.6GY 9.3/1.8 (LRV 83) Munsell color, determined by visual observation.
74. *Fruit sweetness*.—High, reaching 17.5 to 18.0.
75. *Fruit acidity*.—Low, ranging between 0.7 to 1.2% malic acid when fruit is ripe.
76. *Fruit juiciness*.—87% according to Infante et. al. (2009).

Stone:

77. *Stone size compared to fruit*.—Medium, ranging between 10 to 13 g.
78. *Stone shape* (*in lateral view*).—Obovate, similar to 'Rubidoux'. The length is 2.8 cm and width 1.5 cm.
79. *Stone intensity of brown color*.—Medium, classified as in coordinates a*, b* and L* of the CIELab space color (McGuire, 1992) corresponds to 27.5, 16.9, and 7.6, respectively.
80. *Stone relief of surface*.—Pits similar to 'Madame Girard'.
81. *Stone grooves, similar to 'Madame Girard'*.—
82. *Stone tendency of splitting* (*at peak harvest*).—Absent.
83. *Stone adherence to flesh*.—Present, similar to 'Sweet Gold'.
84. *Stone degree of adherence to flesh*.—Strong, similar to 'Vivian'.

Phenology:

85. *Time of leaf bud burst*.—Early, similar to 'Springtime'. On Southern Hemisphere is between $10^{th}$ to $15^{th}$ September.
86. *Time of beginning of flowering*.—Medium, similar to 'Redhaven'. On Southern Hemisphere is between $10^{th}$ to $18^{th}$ August.
87. *Duration of flowering*.—Short, 5-7 days.
88. *Time of maturity for consumption*.—Medium, similar to 'Fairhaven'. On Southern Hemisphere is between $10^{th}$ to $15^{th}$ January.
89. *Tendency to preharvest*.—Absent.
90. *Pest/disease resistance/susceptibility*.—This genotype is not genetically resistant to any common pest and disease of peach, as Mildew, leaf curl, bacterial canker, aphids, thrips or, Oriental moth.

91. Fruit characterization is on table 1.
92. *Regularity of bearing*.—Regular.

TABLE 1

Fruit characterization of nectarine 'Andes Nec-4'

| SEASON | Harvest Date | Blush (%) | Firmness (Lb) Equatorial Diameter | Shoulders | Suture | Tip | Soluble solids (° Brix) |
|---|---|---|---|---|---|---|---|
| 2013-2014 | Jan. 3 | 90 | 13.0 | 12.5 | 13.9 | 12.9 | 18.0 |
| 2014-2015 | Jan. 12 | 100 | 12.0 | 12.7 | 13.0 | 13.6 | 17.2 |
| 2015-2016 | Jan. 7 | 100 | 11.8 | 12.7 | 12.8 | 12.3 | 17.5 |

GENERAL TECHNICAL NOTES

Very good outward appearance. Excellent color coverage. Fruit round, no tip. High productivity. Excellent flavor.

CONCLUSIONS

After four years of evaluation, the variety continues to show its outstanding characteristics: very good productivity, good size, good flavor and good external appearance. High potential for export purposes for Asian countries because of its white flesh and its exceptional post-harvest life potential.

Having thus described and illustrated the new variety of nectarine tree, I claim:

1. A new and distinct variety of nectarine tree, substantially as illustrated and described, that is similar to nectarine '6B-170' by producing nectarines which are white fleshed, but distinguished therefrom by reaching out higher content of soluble solids, by more extended red blush of the nectarine surface, by slower pulp softening rate during the last two weeks before the commercial harvest, by a higher postharvest life potential, and by a balanced acid/sweet flavor.

* * * * *